US00PP23245P2

(12) United States Plant Patent
Danziger

(10) Patent No.: US PP23,245 P2
(45) Date of Patent: Dec. 4, 2012

(54) ***PORTULACA* PLANT NAMED 'DPAZ17'**

(50) Latin Name: *Portulaca oleracea*
Varietal Denomination: DPAZ17

(75) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 38 days.

(21) Appl. No.: 13/068,525

(22) Filed: May 13, 2011

(51) Int. Cl.
*A01H 5/00* (2006.01)

(52) U.S. Cl. ..... Plt./471

(58) Field of Classification Search ..... Plt./471
See application file for complete search history.

*Primary Examiner* — Susan McCormick Ewoldt
(74) *Attorney, Agent, or Firm* — Cassandra Bright

(57) ABSTRACT

A new and distinct *Portulaca* cultivar named 'DPAZ17' is disclosed, characterized by large white flowers. The new variety has a compact, semi trailing growth habit and forms a dense plant. Flowers distinctively open early in the morning, and remain open into the evening hours. The new variety is a *Portulaca*, normally produced as an outdoor garden or container plant.

2 Drawing Sheets

Latin name of the genus and species: *Portulaca oleracea.*
Variety denomination: 'DPAZ17'.

BACKGROUND OF THE INVENTION

The new *Portulaca* cultivar is a product of a planned breeding program conducted by the inventor, Gavriel Danziger, in Moshav Mishmar Hashiva, Israel. The objective of the breeding program was to produce new *Portulaca* varieties for ornamental commercial applications. The cross resulting in this new variety was made during September 2008.

The seed parent is the unpatented, proprietary seedling variety referred to as P*ortulaca oleracea* 'PT-8-425' The pollen parent is unknown, as the crossing resulting in 'DPAZ17' was an open pollination, with unidentifiable pollen parents. The new variety was discovered in July 2009 by the inventor in a group of seedlings resulting from the 2008 crossing, in a research greenhouse in Moshav Mishmar Hashiva, Israel.

Asexual reproduction of the new cultivar 'DPAZ17' by vegetative cuttings was first performed at a research greenhouse in Moshav Mishmar Hashiva, Israel in July 2009 and has shown that the unique features of this cultivar are stable and reproduced true to type in successive generations.

SUMMARY OF THE INVENTION

The cultivar 'DPAZ17' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPAZ17' These characteristics in combination distinguish 'DPAZ17' as a new and distinct *Portulaca* cultivar:

1. Large flowers
2. Compact and dense semi trailing habit
3. Flowers open early in the morning and stay open for more hours
4. Low, spreading growth habit.

Plants of the new cultivar 'DPAZ17' are similar to plants of the seed parent, *Portulaca oleracea* 'PT-8-425' in most horticultural characteristics, however, plants of the new cultivar 'DPAZ17' have a more compact plant habit, and larger flowers. Additionally, the new cultivar has flowers that stay open for more hours than the seed parent.

COMMERCIAL COMPARISON

Plants of the new cultivar 'DPAZ17' are comparable to the commercial variety *Portulaca* 'Summer Stars White', patent status unknown to the inventor after reasonable search. These *Portulaca* varieties are similar in most horticultural characteristics, including flower color and flower form. The new variety 'DPAZ17' differs in having larger flowers, that stay open more hours during the day. Additionally, 'DPAZ17' has a different angle of attachment of the flowers and a more compact and dense plant habit than 'Summer Stars White'.

BRIEF DESCRIPTION OF THE PHOTOGRAPHS

Figure 1:
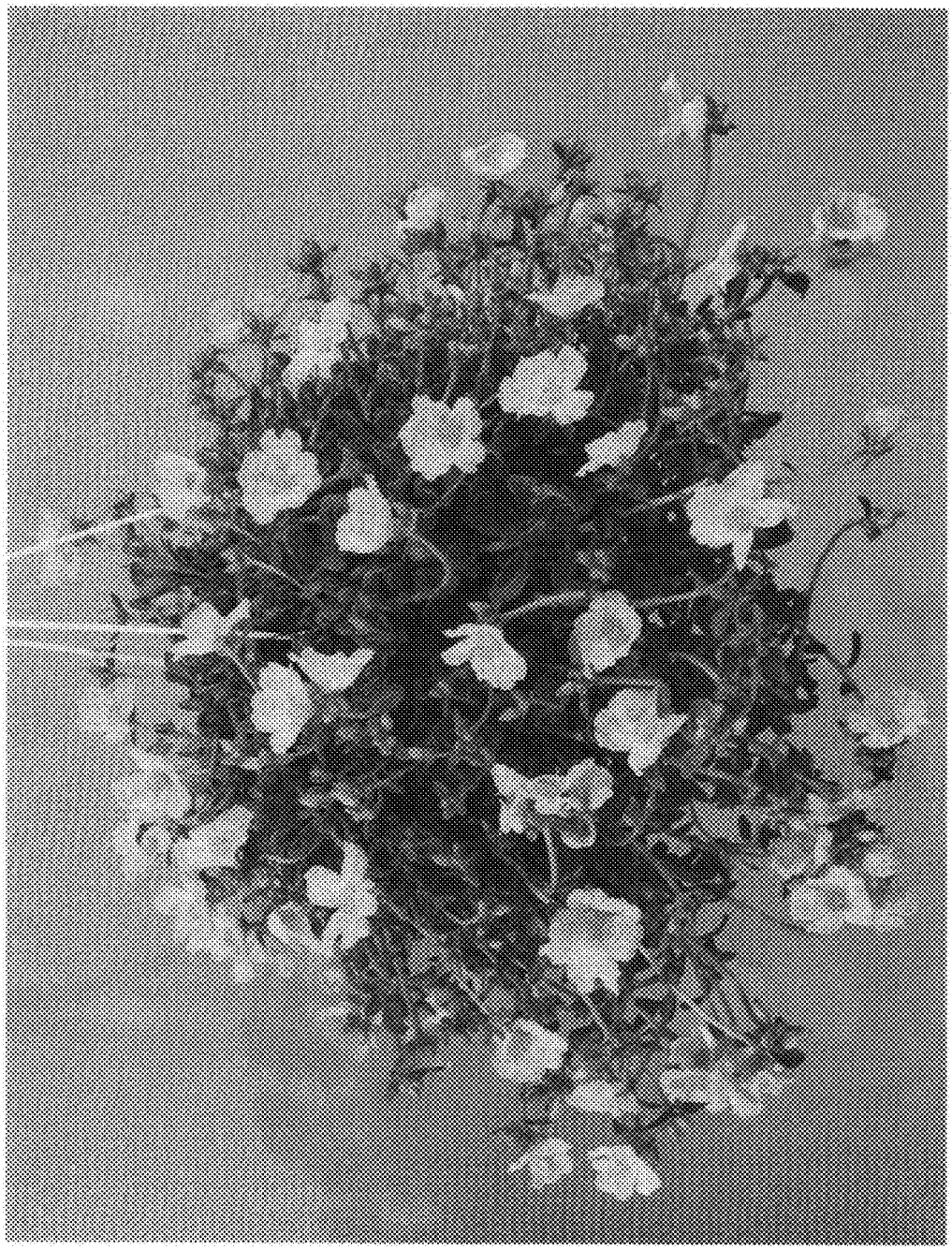

The accompanying photograph in FIG. 1 illustrates in full color a typical plant of 'DPAZ17' grown in a greenhouse, in a 13 cm basket. Age of the plant photographed is approximately 85 days from a rooted cutting.

Figure 2:
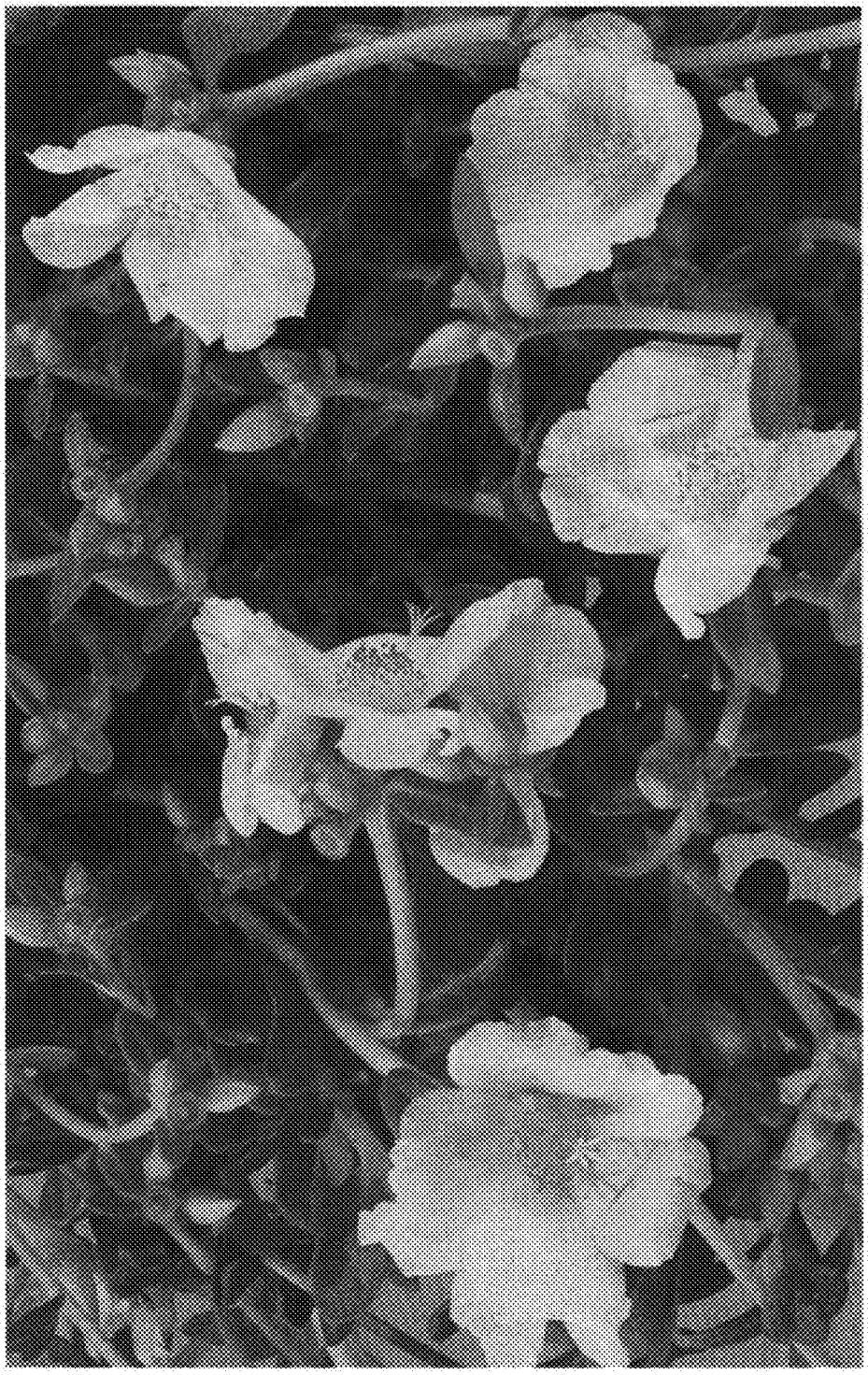

FIG. 2 illustrates in full color a close up of a typical bloom of 'DPAZ17'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DPAZ17' plants grown in a greenhouse during Spring in Gilroy, Calif. The growing temperature ranged from 14° C. to 30° C. during the day and from 10° C. to 23° C. during the night. General light conditions are bright, normal sunlight. Measurements and numerical values represent averages of typical plant types.

Botanical classification: *Portulaca oleracea* 'DPAZ17'.

PROPAGATION

Time to initiate roots: 10 to 14 days at approximately 18-21° C.

Root description: Fibrous, spreading and dense.

PLANT

Age of the plant described: 80 days.

Growth habit: Compact, semi-trailing.

Pot size of plant described: 13 cm.

Height: 15-20 cm.

Plant spread: 35 cm.

Growth rate: Medium vigor.

Branching characteristics: Freely basal branching. Tight, compact, dense plant with lateral branches from each leaf axil.

Length of primary lateral branches: About 27 cm.

Diameter of lateral branches: About 0.3 cm.

Quantity of primary lateral branches: About 8.

Characteristics of primary lateral branches:

*Form*.—Rounded, fleshy with ridges, horizontal.

*Diameter*.—About 0.5 cm.

*Color*.—RHS Green 143C.

*Texture*.—Succulent — smooth, glabrous.

*Strength*.—Moderate.

Internode length: About 2 cm.

FOLIAGE

Leaf:

*Arrangement*.—Alternate.

*Quantity*.—About 12 per main branch.

*Average length*.—About 2.7 cm.

*Average width*.—About 1.2 cm.

*Shape of blade*.—Most of them are obovate shape (mature leaves) and parts are elliptic (young leaves).

*Apex*.—Most mature leaves are rounded, young leaves acute.

*Base*.—Attenuate.

*Margin*.—Entire.

*Texture of top surface*.—Glabrous, smooth.

*Pubescence*.—None.

*Attachment angle*.—At right angle or obtuse angle to stem.

*Color*.—Young foliage upper side: Near RHS Yellow-Green 146B. Young foliage under side: Near RHS Yellow-Green 146B 146C. Mature foliage upper side: Near RHS Green 137C. Mature foliage under side: Near RHS Yellow-Green 146B 147C.

*Venation*.—Type: Pinnate. Venation color upper side: RHS Green 137C. Venation color under side: Approximately RHS Yellow-Green 147C. Venation color is indistinguishable from foliage.

*Petiole*.—Length: 0.15 cm. Diameter: 0.2 cm. Color: Near RHS Green 143C. Texture: Smooth, Glabrous.

FLOWER

Natural flowering season: From Spring to Autumn.

Days to flowering from rooted cutting: Approximately 8 weeks.

Inflorescence and flower type and habit: Terminal, single, sessile. Flower habit horizontal.

Rate of flower opening: 7 to 10 days from bud to fully opened flower.

Flower longevity on plant: Approximately 1 day.

Persistent or self-cleaning: Self-Cleaning.

Bud:

*Shape*.—Ovate with a pointed tip.

*Length*.—Approximately 1.0 cm.

*Diameter*.—Approximately 0.5 cm.

*Color*.—Near RHS Yellow-Green 144A.

Flower size:

*Diameter*.—Approximately 5.2 cm.

Corolla/petals:

*Arrangement*.—Single flower with five distinct overlapping petals.

*Length*.—Approximately 2.3 cm.

*Width*.—Approximately 2 cm.

*Quantity*.—5 petals.

*Texture*.—Glabrous.

*Apex*.—Emarginate.

*Shape*.—Obovate.

*Margin*.—Sinuate.

*Color*.—When opening: Upper surface: Near RHS White N155B. Lower surface: Near RHS White 155B. Fully opened: Upper surface: Near RHS White N155A. Lower surface: Near RHS White N155A.

Calyx/sepals:

*Quantity per flower*.—2.

*Shape*.—Deltoid.

*Length*.—Approximately 0.85 cm.

*Width*.—Approximately 0.8 cm.

*Apex*.—Acute.

*Base*.—Fused.

*Margin*.—Entire.

*Texture*.—Glabrous.

*Color*.—Upper and Lower Surface: Near RHS Yellow-Green 144A.

Peduncle: None.

Fragrance: None.

REPRODUCTIVE ORGANS

Stamens:

*Number*.—About 90.

*Filament length*.—Approximately 0.5 cm.

Anthers: Shape: Oval, bilobed. Length: Approximately 0.5 mm. Color: Near RHS Yellow 13B. Pollen: Color: Near RHSYellow-Orange 23A. Quantity: Abundant.

Pistil:

*Number*.—1 per flower.

*Length*.—Approximately 1.3 cm.

*Style*.—Length: Approximately 1 cm. Color: Near RHS Yellow-Green 145C.

*Stigma*.—Shape: Six-branched. Color: Near RHS White 155A and the center near RHS Yellow-Green 145C. Ovary Color: Near RHS Yellow-Green145B.

OTHER CHARACTERISTICS

Seeds and fruits: Fruits are egg-shaped 4-5 mm long with a conical shape top. Seeds are glossy black with a circular shape.

Disease/pest resistance: Neither resistance nor susceptibility to diseases or insects has been observed.

Temperature tolerance: Will not tolerate temperatures below 7° C.

What is claimed is:

1. A new and distinct cultivar of *Portulaca* plant named 'DPAZ17' as herein illustrated and described.

* * * * *